Figure 1:
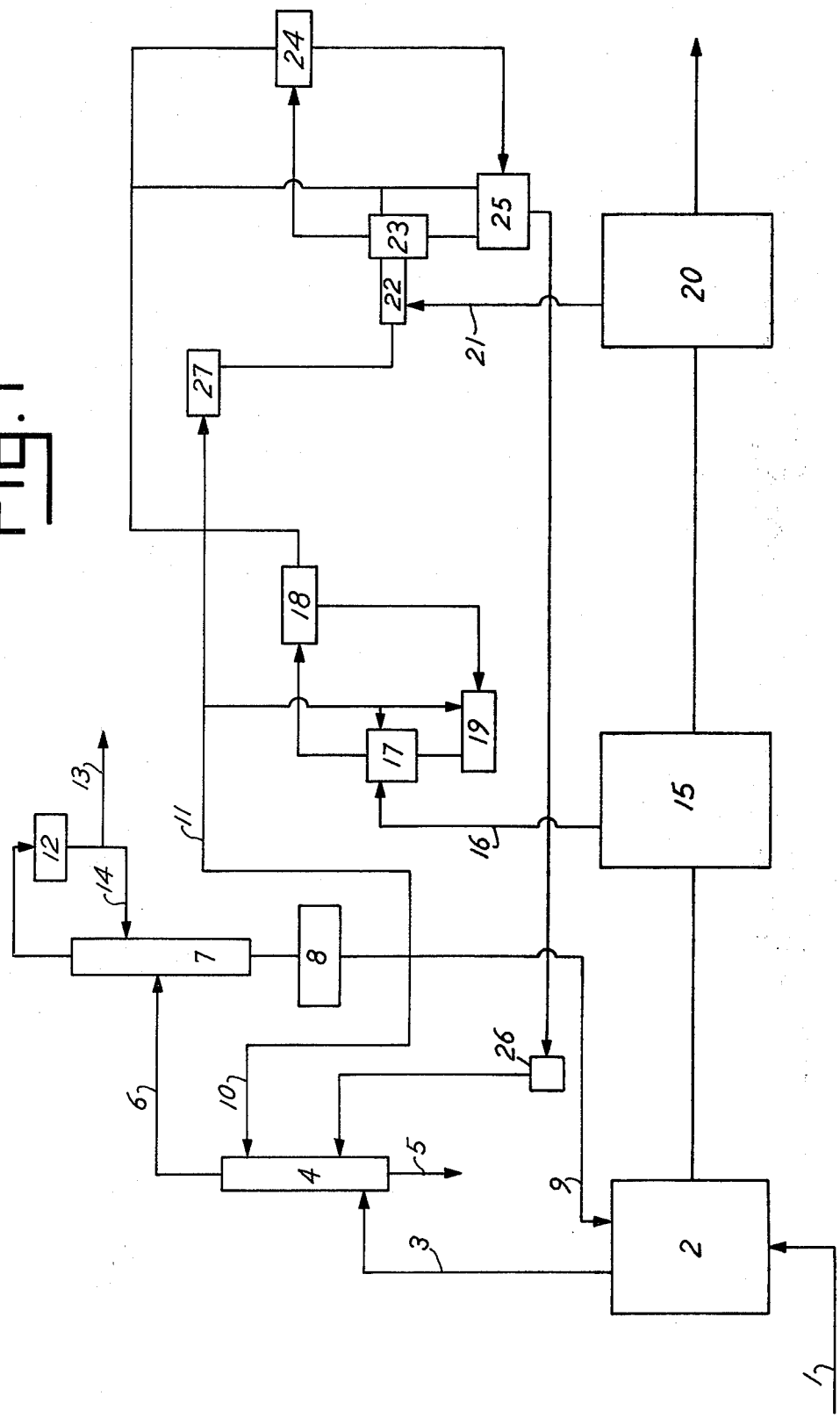

United States Patent [19]

Dicoi et al.

[11] 4,254,246
[45] Mar. 3, 1981

[54] COLUMN SYSTEM PROCESS FOR POLYESTER PLANTS

[75] Inventors: Ovidiu Dicoi, Offenbach am Main; Hans Wewer, Schöeck, both of Fed. Rep. of Germany

[73] Assignee: Davy International AG, Frankfurt am Main, Fed. Rep. of Germany

[21] Appl. No.: 23,831

[22] Filed: Mar. 26, 1979

[51] Int. Cl.³ .............................................. C07C 69/82
[52] U.S. Cl. ...................................... 526/68; 159/31; 203/28; 203/71; 203/DIG. 6; 528/272; 528/309
[58] Field of Search ................... 526/68; 528/308, 309, 528/272; 203/71, 73, 75, 77, 78, 80, 81, 84, 28, DIG. 6; 159/31; 55/32, 31

[56] References Cited

U.S. PATENT DOCUMENTS

| | | | |
|---|---|---|---|
| 3,367,847 | 2/1968 | Pierson | 203/81 |
| 4,146,729 | 3/1979 | Goodley et al. | 526/68 |

Primary Examiner—Frank Sever
Attorney, Agent, or Firm—Allegretti, Newitt, Witcoff & McAndrews

[57] ABSTRACT

A new process for use with continuously operated plants for the production of polyester polymers suitable for producing fibers, bottles and film, by reacting ethylene glycol and terephthalic acid in the presence of a catalyst so that the vapour by-products from the esterification, prepolycondensation and polycondensation stages are continuously rectified in two in-line columns yielding ethylene glycol of high purity (99.85%) which is returned to the process, waste water with 400 ppm ethylene glycol, and a heavy fraction containing oligomers, diethylene glycol, etc.

Moreover, an improvement in the quality of the esterified product is attained as it contains less than 0.6% diethylene glycol without the use of diisopropylamine, a poisonous additive.

8 Claims, 1 Drawing Figure

COLUMN SYSTEM PROCESS FOR POLYESTER PLANTS

BACKGROUND OF THE INVENTION

According to the prior art the vapour by-products from the esterification, prepolycondensation and polycondensation stages consisting of aldehydes, water, ethylene glycol, diethylene glycol and oligomers are treated in various ways.

The vapours from the esterification stages are condensed and cooled from 260°–270° C. to 90°–95° C. in surface condensers. The condenser surfaces are washed with ethylene glycol to prevent the solids collecting. Frequently, the condensers are shut down and the oligomer deposits are melted and removed at high temperature. The necessary excess ethylene glycol in the esterification stages is maintained by feeding a cold EG/TPA paste with a higher mole ratio (1.5 to 1.8).

The ethylene glycol is fed to the esterification stages at 25°–30° C. where it is heated and vapourized at 260°–270° C.; the vapours are then condensed and cooled. Finally the ethylene glycol is recovered from the condensate through successive rectification. This process is very inefficient, has high ethylene glycol and energy consumption, and is carried out in complicated equipment (condensers with stand-by pumps, ethylene glycol recovery plant, hold tanks, etc.).

Because of high heat loads in the first esterification stages the heat exchanger surface has a temperature higher than 275° C. which increases the diethylene glycol formation rate. To prevent this phenomena diisopropylamine (DIPA) is added, an organic base which reduces the acid-catalysed reaction rate of ethylene glycol to form diethylene glycol. Unfortunately DIPA is an undesirable component which changes the colour of the polyester end product and also has a high toxicity.

Other processes using an in-line distillation column have been developed to avoid the above disadvantages. The vapours from the esterification stages are fed into the column bottom that has only a rectifying zone. The overhead vapours are withdrawn from the top of the column and condensed. A portion of the condensate is returned to the top of the column as external reflux and the rest is sent to waste. The bottom product consisting of ethylene glycol contaminated with diethylene glycol and oligomers is returned to the esterification stages.

An enriching column has the function of purifying the lower boiling constituent, water. However, this device is incapable of producing the very pure ethylene glycol bottoms product necessary for the esterification process because even if the column had an infinite number of stages, the bottoms composition would contain 5 wt % water which reduces the rate of the esterification reaction. In order to reduce the water concentration of bottom product to approximately 0.5 wt % the column is operated to produce distillate with 1.4 to 1.6 wt % ethylene glycol. Consequently the high concentration of ethylene glycol in the distillate (1.4–1.6 wt %) produces high losses of ethylene glycol and an unjustified high operating cost for waste water treatment.

Moreover, the ethylene glycol bottom product returning to the esterification process is contaminated with diethylene glycol and oligomers such as diglycol acid mono glycol ester. By recycling this impure ethylene glycol the concentration of diethylene glycol in the esterified product increases by an average of 30 to 40 percent. The presence of significant amounts of diethylene glycol in the esterified product is particularly intolerable for the quality of the end product.

Another disadvantage of all prior processes is that the recovery of ethylene glycol from outgoing vapours of pre- and polycondensation stages is carried out in a complicated distillation plant. The yield of recovered ethylene glycol is only 85–90 percent.

SUMMARY OF THE INVENTION

This invention relates to a new process for separating the ethylene glycol by-products that result by reacting terephthalic acid and ethylene glycol in the presence of any kind of catalysts and catalyst systems for preparation of high molecular weight polyethylene terephthalate suitable for production of fibers, bottles and films.

The separation of all the organic impurities from the crude ethylene glycol is carried out in two in-line columns.

Under steady state conditions the ethylene glycol vapours from the esterification stages are directly fed into the bottom of the first column. At the same time the vapours from the pre- and polycondensation stages are condensed with cooled ethylene glycol and the resulting condensate is fed as reflux to the first column.

The first distillation column has only an enriching zone and is employed to separate the lower boiling components (aldehydes, 2-methyl-1,3-dioxolan) with ethylene glycol as overhead vapours from the heavy components such as diethylene glycol and oligomers.

The overhead ethylene glycol vapours from the esterification stages are charged to the bottom of the first column through a submerged pipe under the liquid surface. The hot ethylene glycol keeps the oligomers in the liquid phase and avoids the settling of agglomerates.

The second feed, consisting of ethylene glycol condensate, is introduced into the first column at a point where the ascending vapours are in equilibrium with the internal reflux. The external reflux consisting of pure ethylene glycol from the bottom of the second column is fed continuously to the column near the top thereof. The internal reflux is very concentrated in ethylene glycol and is of sufficient quantity to decrease the volatility of diethylene glycol.

The residual portion of internal liquid reflux withdrawn from the bottom is a solution of oligomers in ethylene glycol and diethylene glycol. The bottom product contains approximately 30–40 wt % ethylene glycol which makes it possible to obtain an overhead product with less than 0.01 wt % diethylene glycol.

The overhead vapours from the first column are charged to the second column which has a rectification zone and a stripping zone.

The internal liquid reflux, including ethylene glycol, flows in a downward direction through the stripping zone. The stripping zone has sufficient contact stages to strip the liquid reflux of all low boiling compounds which are rendered more volatile than the ethylene glycol.

The residual liquid reflux reaches the bottom of the stripping zone and is passed to a reboiler for heating. A heated and vapourised portion of the bottom product is recycled from the reboiler back to the lower part of the column. A portion of the bottom liquid is introduced as reflux into the first column. The residual portion, containing pure ethylene glycol is metered back to the process. The overhead vapours containing aldehydes, water and approximately 400 ppm ethylene glycol passes through a cooling condenser. A portion of the distillate is returned as external reflux to the upper part of the column. A remaining portion of the distillate is withdrawn as waste water. The internal liquid reflux of the enriching zone is very concentrated in water allowing only traces of ethylene glycol to be retained in the phase.

Before reaching the feed plate, the temperature and the quantity of the internal liquid reflux is adjusted with distillate so that the ethylene glycol from ascending vapours is condensed and returned to the stripping zone. The pure ethylene glycol from the bottom of the second column containing less than 0.01 wt % diethylene glycol is fed direct to the esterification stages and to the vacuum units.

The system utilizing the invention offers the following advantages over the hitherto employed systems:
- Low consumption of ethylene glycol for production of polyethylene terephthalate. This is attained by a higher yield of 99% in recovered ethylene glycol.
- Elimination of capital investment and conversion costs attributable to use of separate ethylene glycol recovery plants in prior processes.
- A substantial reduction in the environmental pollution due to a very low ethylene glycol content of approximately 400 ppm in the effluent, which in turn will result in a reduction in the load on the water treatment plant.
- Entire quantity of ethylene glycol recycled back to the process has a very high purity of 99.85 wt %. The prior processes that employ one process column and a separate ethylene glycol recovery plant are able to rectify only 30% from entire ethylene glycol by-product.
- Improvement in the quality of the esterified product by reducing to below 0.6 wt % the diethylene glycol content that is obtained by removing the evaporated diethylene glycol and oligomers from the esterification stages.

SPECIFIC EXAMPLE

A process column system for a continuously operated polyester plant in accordance with the invention is shown in the accompanying drawing.

A continuous polyester plant consisting basically of esterification 2, precondensation 15 and polycondensation 20 reactors, glycol contact condensers 17, 23, ejectors 22 using glycol vapours as the motive fluid, and glycol vacuum ring pump 18, 24 is provided with two column 4, 7 to process all glycol effluents.

A homogeneous past of EG/TPA, having an EG/TPA mole ratio of 1.15–1.3, with a catalyst, e.g. antimony triacetate, germanium oxide, is pumped at a rate of 6110 kg/h into the esterification stage 2 via line 1. Glycol vapours are released from 2 and via line 3 are fed into the column 4 at a rate of 2280 kg/h, 260° C. and 1.15–1.30 bar. This by-product of the esterification process consists of low boiling components (aldehyde, 2-methyl-1,3-dioxolan), water, ethylene glycol, diethylene glycol and oligomers.

The esterification product, containing 0.52 wt % diethylene glycol, from 2 is fed into reactor 15 where, at a temperature of 272°–277° C. and 250–50 mbar, the precondensation process takes place until the intrinsic viscosity increases to 0.14–0.20. The overhead EG vapours resulting during the precondensation reaction, consisting of aldehydes, water, ethylene glycol, diethylene glycol and oligomers, are fed via line 16 into condenser 17 and condensed with cooled EG. The residual vapours from 17 are sucked to the vacuum ring pump 18 and further condensed by glycol. Condensed EG from the bottom of 17 and from 18 is collected in 19.

The precondensate is transferred from 15 into reactor 20 where the polycondensation process in continued until the intrinsic viscosity increases to 0.6–0.75. The melted polymer leaves the polycondensation reactor 20 at a temperature of 277°–280° C. The high vacuum 1–2 mbar necessary for removing spent glycol is produced by means of glycol ejectors 22 and vacuum ring pumps 24. The vapours of spent glycol are removed via line 21 by means of 22 using EG vapours as motion fluid; these vapours are partially condensed together in 23 with cooled EG. The noncondensable vapours from 23 are further condensed in the EG of vacuum ring pump 24. The EG condensate that results from 23, 24 is collected in vessel 25. The crude EG from 19 and 25 is preheated to 160°–180° C., and fed into the column 4 by means of pump 26 at a rate of 435 kg/h with the following composition:

| low boiling components | 2.19 wt % |
| water | 8.97 wt % |
| ethylene glycol | 86.09 wt % |
| diethylene glycol | 0.75 wt % |
| oligomers | 2.00 wt % |

The bottom product of column 4 passes via line 5 at 61 kg/h and 200°–218° C. to an incinerator. This product is a mixture of heavy components with the following composition:

| ethylene glycol | 40 wt % |
| diethylene glycol | 16 wt % |
| oligomers | 44 wt % |

The overhead vapours which pass from column 4 are fed via line 6 at 168° C. and 1.02–1.61 bar into column 7. This overhead product has the following composition:

| low boiling components | 0.3 wt % |
| water | 28 wt % |
| ethylene glycol | 71 wt % |
| diethylene glycol | 100 ppm |
| oligomers | 0.69 wt % |

The bottom product of the column 7 is ethylene glycol of 99.85 wt % purity. This product is collected in the hold tank 8 at a rate of 2553 kg/h and 192° C. The pure EG from 8 is pumped at 1326 kg/h into the esterification stages 2 via line 9 and at a rate of 886 kg/h is returned as reflux into column 4 via line 10, after cooling to approximately 160°–170° C. The residue of pure EG is pumped via line 11 into either the glycol evaporator 27 or the condensers 17, 23 or vacuum ring pumps 18, 24 after cooling to normal temperature. The overhead products from column 7, consisting of water with approximately 400 ppm glycol, is condensed in 12; 987 kg/h is discharged via line 13 as waste water, the remainder is recycled to column 7 via line 14 at a reflux ratio of 0.5.

We claim:

1. A continuous process for purifying and recovering at least 99% ethylene glycol from the vapour by-products generated in three reactors (esterification, prepolycondensation and polycondensation) during the reaction of ethylene glycol and terephthalic acid to produce polyethylene glycol terephthalate polymer, said by-products being contamined with aldehydes, water, diethylene glycol and oligomers, which comprises:

(a) providing an enriching column and a rectification column, (b) introducing a first stream of ethylene glycol vapours from the esterification stage into the bottom of said enriching column, said first stream containing at least about 90% ethylene glycol, (c) introducing a second stream of ethylene glycol condensate from the pre- and polycondensation reactors into said enriching column above said first stream for flow countercurrent to the upward flow of said first stream, thereby condensing said diethylene glycol and oligomers, (d) removing the resulting mixture of ethylene glycol, diethylene glycol and oligomers from the bottom of said enriching column at a rate which maintains some liquid in the bottom of said column into which liquid said first stream is introduced, (e) charging the resulting mixture of aqueous ethylene glycol vapour and aldehydes rising from the top of said enriching column into said rectification column, (f) condensing a portion of said aqueous ethylene glycol vapour and refluxing the condensate in the rectification column to condense ethylene glycol from said aqueous ethylene glycol vapour, (g) removing from the top of said rectification column a portion of said aqueous vapours containing less than 440 ppm ethylene glycol, condensing the vapours and discharging the condensate directly to waste, (h) withdrawing from the bottom of said rectification column ethylene glycol of at least 99.85% purity, and (i) recycling at least a portion of said pure ethylene glycol directly into said esterification reactor.

2. The process of claim 1 in which said refluxing condensate of step (f) is a portion of aqueous ethylene glycol vapour discharged from the top of the rectification column.

3. The process of claim 1 in which another portion of pure ethylene glycol is charged into said enriching column above said second stream.

4. The process of claim 3 in which said second stream contains at least 90% ethylene glycol and said another portion of pure ethylene glycol is maintained at a temperature below about 170° C. to condense traces of diethylene glycol in the ascending aqueous vapour mixture and reduce the diethylene glycol content to less than 100 ppm.

5. The process of claim 3 in which said another portion of pure ethylene glycol is charged between 160° and 170° C. and at a ratio of 0.2 to 0.4 with respect to the quantity of ethylene glycol in said stream.

6. The process of claim 1 in which said ethylene glycol condensate of step (c) is condensed prior to forming said second stream by contacting with pure ethylene glycol from step (g).

7. The process of claim 6 in which said contacting step is carried out under vacuum and said pure ethylene glycol is a motion fluid for carrying the vapours from the pre- and polycondensation reactors through said contacting step.

8. The process of claim 1 in which the pressure prevailing in said prepolycondensation reactor ranges from 250–50 mbar and in said polycondensation reactor from 1–2 mbar.

* * * * *